US00PP36355P3

(12) United States Plant Patent
Schoone

(10) Patent No.: US PP36,355 P3
(45) Date of Patent: Dec. 31, 2024

(54) ***PHALAENOPSIS* PLANT NAMED 'Soulmate'**

(50) Latin Name: *Phalaenopsis hybrida*
Varietal Denomination: Soulmate

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/625,189

(22) Filed: Apr. 2, 2024

(65) Prior Publication Data

US 2024/0334857 P1 Oct. 3, 2024

Related U.S. Application Data

(60) Provisional application No. 63/456,505, filed on Apr. 2, 2023.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02; A01H 5/00; A01H 6/62
See application file for complete search history.

(56) References Cited

U.S. PATENT DOCUMENTS

PP30,688 P3 * 7/2019 Schoone ..... A01H 6/62
Plt./311

OTHER PUBLICATIONS

CPVO Register Version 4.20.3 retrieved on Jul. 25, 2024 at https://online.plantvarieties.eu/publicConsultationDetails?registerId=20230526&denomination=soulmate 2 pp. (Year: 2024).*

* cited by examiner

*Primary Examiner* — June Hwu
(74) *Attorney, Agent, or Firm* — C. Anne Whealy

(57) ABSTRACT

A new and distinct cultivar of *Phalaenopsis* plant named 'Soulmate', characterized by its upright plant habit; moderately vigorous growth habit; strong flowering stems; strong leaves; freely flowering habit with typically two or three inflorescences developing per plant, each inflorescence with numerous flowers; flowers with reddish purple-colored petals with white-colored centers; and good postproduction longevity.

2 Drawing Sheets

Figure 1:
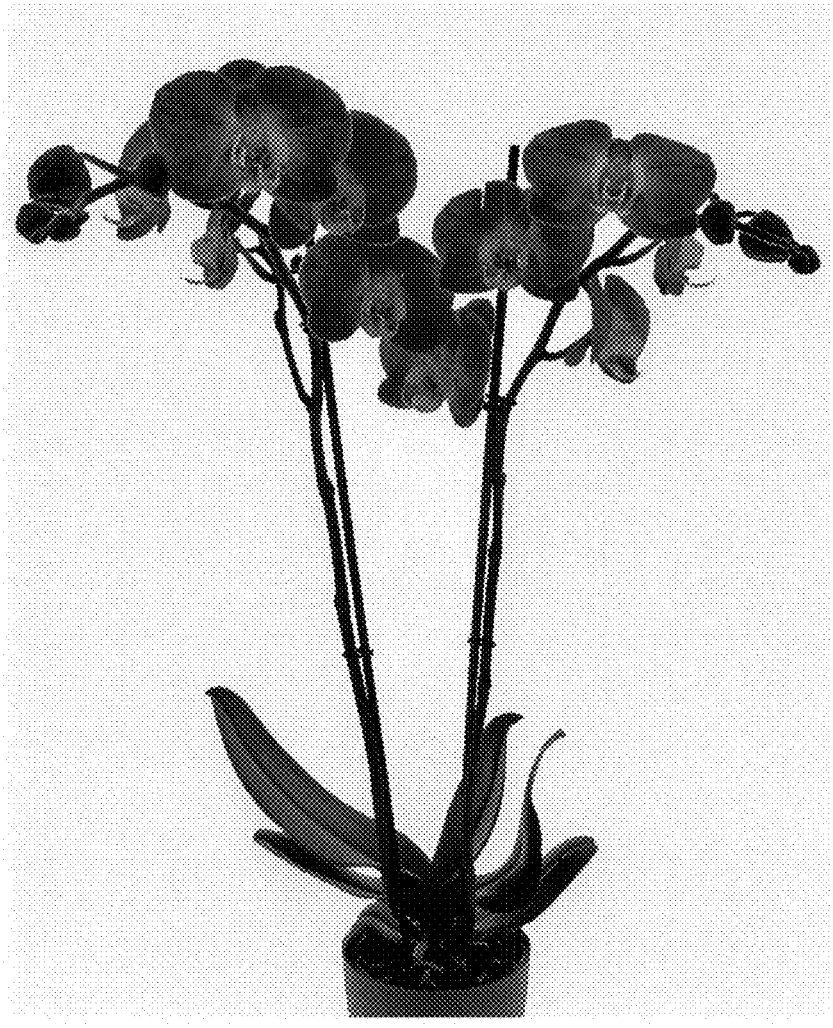

Botanical designation: *Phalaenopsis hybrida.*
Cultivar denomination: 'SOULMATE'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B.V. of Heemskerk, The Netherlands on Feb. 27, 2023, application number 2023/0526. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida,* and hereinafter referred to by the name 'Soulmate'.

The new *Phalaenopsis* plant is a product of a planned breeding program conducted by the Inventor in De Lier and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in December 2012 in De Lier, The Netherlands of a proprietary selection of *Phalaenopsis hybrida* identified as code number 503126, not patented, as the female, or seed, parent with a proprietary selection of *Phalaenopsis hybrida* identified as code number 193634, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in June, 2019.

Asexual reproduction of the new *Phalaenopsis* plant by in vitro meristem propagation in a controlled environment in Assendelft, The Netherlands since June, 2020 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Soulmate'. These characteristics in combination distinguish 'Soulmate' as a new and distinct *Phalaenopsis* plant:

1. Upright plant habit.
2. Moderately vigorous growth habit.
3. Strong flowering stems.
4. Strong leaves.
5. Freely flowering habit with typically two or three inflorescences developing per plant, each inflorescence with numerous flowers.
6. Flowers with reddish purple-colored petals with white-colored centers.
7. Good postproduction longevity.

Plants of the new *Phalaenopsis* can be compared to plants of the female parent selection. Plants of the new *Phalaenopsis* differ primarily from plants of the female parent selection in petal color as petals of plants of the new *Phalaenopsis* are reddish purple in color whereas petals of plants of the female parent selection are white in color. In addition, the petals of plants of the new *Phalaenopsis* are close to imbricate whereas the petals of plants of the female parent selection are "free" and not imbricate.

Plants of the new *Phalaenopsis* can be compared to plants of the male parent selection. Plants of the new *Phalaenopsis* differ primarily from plants of the male parent selection in petal color as petals of plants of the new *Phalaenopsis* are reddish purple in color whereas petals of plants of the male parent selection are dark purple in color.

Plants of the new *Phalaenopsis* can be compared to plants of *Phalaenopsis hybrida* 'Tigris', disclosed in U.S. Plant Pat. No. 30,688. In side-by-side comparisons, plants of the new *Phalaenopsis* differ primarily from plants of 'Tigris' in the following characteristics:

1. Petals of plants of the new *Phalaenopsis* are close to imbricate whereas the petals of plants of 'Tigris' are "free" and not imbricate.
2. Labellum of plants of the new *Phalaenopsis* are white, reddish purple and yellow in color whereas the labellum of plants of 'Tigris' is violet and purplish red in color. Cirrhose tips of the labellum of plants of the new *Phalaenopsis* are white in color whereas cirrhose tips of the labellum of plants of 'Tigris' are violet in color.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet FIG. 1 is a side perspective view of a typical flowering plant of 'Soulmate' grown in a container.

Figure 2:
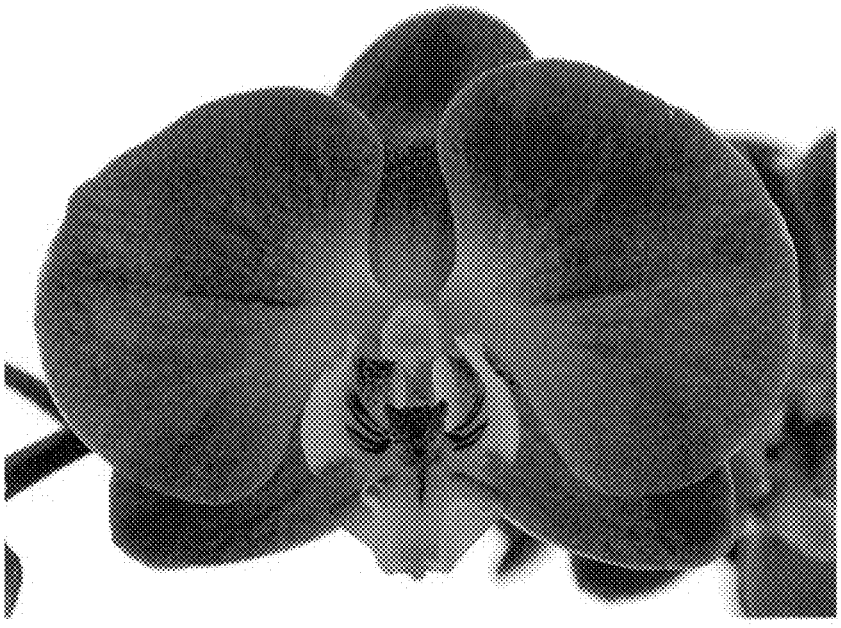

The photograph on the second sheet FIG. 2 is a close-up view of a typical flower of 'Soulmate'.

DETAILED BOTANICAL DESCRIPTION

The aforementioned photographs and following observations and measurements describe plants grown during the winter in 12-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Soulmate'.

Parentage:

*Female, or seed, parent.*—Proprietary selection of *Phalaenopsis hybrida* identified as code number 503126, not patented.

*Male, or pollen, parent.*—Proprietary selection of *Phalaenopsis hybrida* identified as code number 193634, not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two or three inflorescences developing per plant, each inflorescence with numerous flowers; monopodial; moderately vigorous growth habit and moderate growth rate.

*Plant height, substrate level to top of foliar plane.*—About 18.8 cm.

*Plant height, substrate level to top of floral plane.*—About 53 cm.

*Plant diameter or spread.*—About 33.9 cm.

Leaf description:

*Arrangement and quantity.*—Distichous, simple; sessile; about three fully-developed leaves per plant.

*Length.*—About 20 cm.

*Width.*—About 7.7 cm.

*Aspect.*—Semi-erect.

*Shape.*—Narrowly elliptic-oblong to narrowly oblong-obovate; slightly to moderately carinate; apex is slightly to moderately reflexed.

*Apex.*—Unequal acute.

*Base*.—Sheathing. Sheath length: About 1.7 cm. Sheath width: About 1.6 cm. Sheath color: Close to 143B with margins, close to 143A.

*Margin*.—Entire; not undulate.

*Texture and luster, upper surface*.—Smooth, glabrous; moderately glossy.

*Texture and luster, lower surface*.—Smooth, glabrous; slightly glossy.

*Venation pattern*.—Camptodromous.

*Color*.—Developing leaves, upper surface: Darker than a blend of NN137A and 147A. Developing leaves, lower surface: Close to 146A; margins, strongly tinged with close to N186B. Fully expanded leaves, upper surface: Close to NN137A; margins, close to 137C; venation, close to 139A. Fully expanded leaves, lower surface: Close to a blend of 146A and 146B; towards the margins, close to 137B; venation, close to 143A.

Inflorescence description:

*Appearance and flowering habit*.—Showy zygomorphic flowers arranged on axillary simple or branched racemes; typically two or three inflorescences develop per plant; each inflorescence with about ten flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 22.9 cm.

*Inflorescence width*.—About 13.9 cm.

*Flower buds*.—Height: About 1.9 cm. Diameter: About 1.5 cm by 1.8 cm. Shape: Broadly ovate. Color: Close to N186D; towards the base, close to 186A and at the base, tinged with close to 146D.

*Flower size*.—About 7.1 cm (vertical) by 8.7 cm (horizontal). Flower depth: About 3.4 cm.

*Petals, quantity and arrangement*.—Three, two lateral petals and one center petal transformed into a labellum.

*Lateral petals*.—Length: About 4.2 cm. Width: About 5.5 cm. Shape: Broadly deltoid-reniform to close to lunate. Apex: Rounded. Margin: Entire; not undulate. Texture and luster, upper and lower surfaces: Smooth, glabrous; moderately velvety; matte. Color: When opening, upper surface: Close to a blend of N78B, N78C and NN78C; towards the base, close to NN155B and at the base, close to 155A; main vein, close to a blend of N78A and NN78A. When opening, lower surface: Close to N78B to N78D; towards the center, close to a blend of 75B and 76A; towards the base, close to 155C and at the base, close to 77B; venation, close to 77A and 77B. Fully opened, upper surface: Close to a blend of N78B and NN78B; towards the base, close to NN155D and at the base, close to N78D; main vein, close to N78A. Fully opened, lower surface: Close to N78B and a blend of N78B and N78C; towards the center, close to a blend of N75A and N78D; towards the base, close to NN155D and at the base, close to N78B; venation, close to 77B.

*Labella*.—Appearance: Three-parted with two lateral lobes and a central lobe. Length, lateral lobes: About 2.2 cm. Width, lateral lobes: About 1.6 cm. Length, central lobe: About 2.3 cm. Width, central lobe: About 0.6 cm to 2.2 cm. Length, cirrhose tips: About 1.3 cm. Shape, lateral lobes: Obovate. Shape, central lobe: Deltoid with an elongated apex. Apex, lateral lobes: Obtuse. Apex, central lobe: Cleft with two upward and backwardly curled cirrhose tips. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 5 mm in length, about 7 mm in width and about 7 mm in height. Color: When opening, upper surface: Lateral lobes: Close to NN155D; lower margins, close to 4C; at the base, axial stripes, close to 71A and 71B. Central lobe: Close to 75B; towards the base, close to 1C with edges, close to 64B, and at the base, close to 155C with stripes, close to N186D; main vein, dotted with close to N186D; cirrhose tips, close to 157D. When opening, lower surface: Lateral lobes: Close to NN155D; lower margins, close to 4C; at the base, slightly tinged with close to 183D. Central lobe: Close to N75A; towards the apex, close to 77B; towards the margins, close to 76B; towards the base, close to 146D and at the base, close to 157A; cirrhose tips, close to 157D. Fully opened, upper surface: Lateral lobes: Close to NN155D; upper margins, tinged with close to a blend of N78C and NN78D; lower margins, close to 12B with edges, close to 185B; at the base, axial stripes, close to 71B. Central lobe: Close to 75A; towards the base, close to 10B with edges, close to 181B, and at the base, close to NN155C with stripes, close to N186D; main vein, tinged with close to 10C and finely dotted, close to N186D; cirrhose tips, close to 155A. Fully opened, lower surface: Lateral lobes: Close to NN155D; upper margins, tinged with close to a blend of N78C and NN78D; lower margins, close to 12B with edges, close to 185B. Central lobe: Close to 77B; towards the apex, close to N78B; towards the margins, close to N75C; towards the base, close to 160B and 160C with edges, close to 181B and 181C and at the base, close to 157A; cirrhose tips, close to 155A. Callosities: When developing: Close to 155C; apex, close to 3C with fine dots, close to N186D; inner surface, stripes, close to N186D. Fully developed: Close to 155C; apex, close to 12A with fine dots, close to N186D; inner surface, stripes, close to N186D.

*Sepals*.—Quantity and arrangement: Three, one upper dorsal sepal and two lower lateral sepals. Length, dorsal sepal: About 4.1 cm. Width, dorsal sepal: About 3.3 cm. Length, lateral sepals: About 4.2 cm. Width, lateral sepals: About 3 cm. Shape, dorsal sepal: Broadly elliptic. Shape, lateral sepals: Ovate. Apex, dorsal sepal: Obtuse. Apex, lateral sepals: Bluntly acute. Base, dorsal and lateral sepals: Truncate. Margins, dorsal and lateral sepals: Entire, occasionally with a single shallow incision; not undulate.

Texture and luster, dorsal and lateral sepals, upper and lower surfaces: Smooth, glabrous; moderately velvety; matte. Color, dorsal sepal: When opening, upper surface: Close to N78B; towards the apex, close to N78C; towards the base, close to 76B and 76C; venation, close to N78B. When opening, lower surface: Close to N78B; centers, close to N77B; venation, close to a blend of N77A and N77B. Fully opened, upper surface: Close to a blend of N78A and NN78B; towards the apex, close to N78B; towards the base, close to 76A and 76B. Fully opened, lower surface: Close to NN78B; venation, close to a blend of N78A and NN78A. Color, lateral sepals: When opening, upper surface: Close to a blend of N78B and NN78C; towards the base, close to 76C and at the base, close to a blend of 145C and 150C and a blend of 145D and 150D; fine dots, close to 71A; venation, close to N78A and N78B. When opening, lower surface: Close to N78B; centers, close to N77B; towards the base, tinged with close to 145C and 145D; venation, close to a blend of N77A and N77B. Fully opened, upper surface: Close to NN78B; towards the base, close to N75A and at the base, close to 145C; fine dots, close to 72A; venation, close to NN78A and NN78B. Fully opened, lower surface: Close to N78C to N78D and a blend of N78B and NN78B; centers, close to 72B; at the base, tinged with close to 157A; venation, close to 72A.

*Peduncles*.—Length: About 60.3 cm. Diameter: About 6.5 mm. Strength: Strong. Aspect: Upright to outwardly arching. Texture and luster: Smooth, glabrous; matte. Color: Slightly darker than 147A densely covered with fine dots, close to 138B.

*Pedicels*.—Length: About 4.2 cm. Diameter: About 3.5 mm. Strength: Moderately strong. Aspect: About 90° from peduncle axis. Texture and luster: Smooth, glabrous; matte. Color: Close to N148C; proximally, tinged with close to a blend of N186C and 200A; distally, tinged with close to 182D.

*Reproductive organs*.—Androecium: Column length: About 9 mm. Column width: About 6 mm. Column color: Close to NN155D; distally, slightly tinged with close to N155B. Pollinia quantity: Two. Pollinia diameter (per two pollinia): About 3 mm. Pollinia color: Close to N25B. Gynoecium: Stigma length: About 3 mm. Stigma width: About 5 mm. Stigma shape: Reniform. Stigma color: Close to 157D. Ovary length: About 2 cm. Ovary diameter: About 1 mm. Ovary color: Close to 149C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Soulmate' as herein illustrated and described.

* * * * *